United States Patent
Gündel (10) Patent No.: US 8,577,102 B2
(45) Date of Patent: Nov. 5, 2013

(54) METHOD FOR IMPROVING THE ACCURACY OF A BRONCHIAL BIOPSY, AND DEVICE FOR CARRYING OUT A METHOD FOR IMPROVING THE ACCURACY OF A BRONCHIAL BIOPSY

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1375 days.

(21) Appl. No.: 11/878,826

(22) Filed: Jul. 27, 2007

(65) Prior Publication Data
US 2008/0027354 A1 Jan. 31, 2008

(30) Foreign Application Priority Data

Jul. 28, 2006 (DE) .......................... 10 2006 035 123

(51) Int. Cl.
*G06K 9/00* (2006.01)
*A61B 5/05* (2006.01)

(52) U.S. Cl.
USPC ............................. 382/128; 600/407; 600/562

(58) Field of Classification Search
USPC ......... 382/100, 128–132, 154, 168, 173, 181,
382/194, 199, 224, 232, 254, 276, 305;
128/920, 922; 434/262, 267; 700/57,
700/245; 703/2, 6, 11; 606/1, 45, 130, 159;
600/101, 109, 112, 114, 117–118, 139,
600/145, 173, 420, 424, 427, 434, 415–416,
600/562, 587; 378/21; 345/419, 424
See application file for complete search history.

(56) References Cited

U.S. PATENT DOCUMENTS

| | | | | |
|---|---|---|---|---|
| 5,681,327 A | * | 10/1997 | Heywang-Koebrunner | . 606/130 |
| 7,179,220 B2 | * | 2/2007 | Kukuk | 600/101 |
| 7,277,833 B2 | * | 10/2007 | Kukuk | 703/2 |
| 2002/0133057 A1 | * | 9/2002 | Kukuk | 600/101 |
| 2003/0065260 A1 | * | 4/2003 | Cheng et al. | 600/427 |
| 2003/0199785 A1 | * | 10/2003 | Hibner et al. | 600/562 |
| 2005/0107679 A1 | | 5/2005 | Geiger et al. | |
| 2006/0052693 A1 | * | 3/2006 | Tynes et al. | 600/424 |
| 2006/0084860 A1 | | 4/2006 | Geiger et al. | |
| 2008/0103387 A1 | * | 5/2008 | Gross | 600/424 |

FOREIGN PATENT DOCUMENTS

DE    11 2004 001 177 T5    6/2006

OTHER PUBLICATIONS

Kiraly, A.P. et al.: << Three-Dimensional Path Planning for Virutal Bronchoscopy IEEE Trans. on Medical Imaging, IEEE, Sep. 2004 vol. 23, No. 9, pp. 1365-1379.
Helferty, J.P. et al.: Image Guided Endoscopy for Lung-Cancer Assessment Proc. IEEE Int. Conf. Image Processing, IEEE, Oct. 2001 pp. 307-310.

* cited by examiner

*Primary Examiner* — Hadi Akhavannik
*Assistant Examiner* — Mehdi Rashidian
(74) *Attorney, Agent, or Firm* — Harness, Dickey & Pierce, P.L.C.

(57) ABSTRACT

A method is disclosed for improving the accuracy of a bronchial biopsy. In at least one embodiment, the method includes detecting the position and extent of a lesion to be biopsied by way of imaging methods, calculating the maximum biopsy depth with a known biopsy inaccuracy as a function of the extent of the lesion, and producing a biopsy plan on the basis of the calculated maximum biopsy depth and the position of the lesion. A device is also disclosed for carrying out the method.

24 Claims, 5 Drawing Sheets

METHOD FOR IMPROVING THE ACCURACY OF A BRONCHIAL BIOPSY, AND DEVICE FOR CARRYING OUT A METHOD FOR IMPROVING THE ACCURACY OF A BRONCHIAL BIOPSY

PRIORITY STATEMENT

The present application hereby claims priority under 35 U.S.C. §119 on German patent application number DE 10 2006 035 123.1 filed Jul. 28, 2006, the entire contents of which is hereby incorporated herein by reference.

FIELD

The present application relates in general to the biopsy of lesions that lie directly on the bronchi, such as are applied in medicine to examine patients for example. For example, the present application relates, in particular, to a method for carrying out such an examination in the case of which the accuracy of the biopsy can be improved.

BACKGROUND

When diagnosing pulmonary foci or in the case of lesions of the mediastinum, frequently requires carrying out a biopsy of the affected region. It is only by the removal of tissue that it can be unambiguously established whether the lesion is benign or malignant, and which therapy measures need be taken, if appropriate. This is predominantly carried out percutaneously (through the skin). Disadvantages of this method are the low hit rate of centrally positioned lesions, together with the time consuming repetition, associated therewith and increasing the risk to the patient, of the procedure, as well as the so called pneumothorax, in which air penetrates through the thorax. The pressure arising at the lung complicates breathing and must be treated in many instances.

For this reason, lesions lying directly on the bronchi and that are of sufficient size are better biopsied transbronchially. In this case, use is made of a special bronchoscope having a channel for visualization and a working channel for removing a tissue sample. If the lesions on the inner bronchial wall can be identified, good results can be obtained thereby. On the other hand, uncertainty arises during the biopsy as to whether the lesion has really been hit. If the tissue sample removed is malignant, it is simultaneously an indication that the lesion has been hit. However, if this is not the case, either the lesion is benign or it has not been hit, and the biopsy must be repeated.

An improvement is delivered here by a method such as is proposed in document US 2006/0084860 A1. Here, imaging methods are used to carry out a segmentation of the bronchi, and thereby to produce a three-dimensional virtual image of the bronchi. During the carrying out of the bronchoscopy, the lesion on the inner surface of the bronchial wall is inserted on this three-dimensional virtual representation of the bronchi, and at the same time the current position of the bronchoscope is illustrated in the virtual three-dimensional representation. It is thereby possible to raise the hit probability during the bronchoscopy.

It is, however, disadvantageous in this method that a reliable biopsy is not yielded despite the insertion of the lesion on the inner bronchial wall. Particularly in the case of small lesions, or ones that lie very far removed from the bronchial wall, it is not possible to establish with certainty whether the lesion is benign in the case of a benign tissue sample, or simply has not been hit.

SUMMARY

In at least one embodiment of the present invention, a method is provided for improving the accuracy of a bronchial biopsy, and a device is provided in at least one embodiment for example, for carrying out the method, in which case it can already be determined in the run up to the biopsy whether the lesion can be hit or not with the aid of the biopsy to be carried out.

In accordance with at least one embodiment of the present invention, a method is for improving the accuracy of a bronchial biopsy is proposed, the method comprising:
a) detecting the position and extent of a lesion to be biopsied by way of imaging methods,
characterized by
b) calculating the maximum biopsy depth with a known biopsy inaccuracy as a function of the extent of the lesion, and
c) producing a biopsy plan on the basis of the calculated maximum biopsy depth and the position of the lesion.

In at least one embodiment, Step c) advantageously includes comparing the calculated maximum biopsy depth with the biopsy depth actually required for carrying out the biopsy.

Furthermore, step c) advantageously includes determining a suitable bronchial branch for carrying out the biopsy when the actual biopsy depth required for carrying out the biopsy does not exceed the calculated maximum biopsy depth.

Furthermore, in at least one embodiment, step c) advantageously includes the outputting of a message to the examiner when the actual biopsy depth required for carrying out the biopsy exceeds the calculated maximum biopsy depth.

In at least one embodiment, the biopsy inaccuracy is advantageously determined once by way of test series.

Furthermore, there is advantageously a renewed determination of the biopsy inaccuracy in conjunction with variation of the examination conditions.

In at least one embodiment, the method preferably includes determination of the biopsy inaccuracy by determining a translational error and an angular error in the biopsy, the translational error being a deviation of the actual biopsy point from the ideal biopsy point, and the angular error being a deviation of the actual biopsy direction from the ideal biopsy direction.

In an advantageous refinement of at least one embodiment, step b) comprises:
I) calculating a first maximum biopsy depth as a function of a first extent of the lesion along a first direction parallel to the bronchial wall,
II) calculating a second maximum biopsy depth as a function of a second extent of the lesion along a second direction orthogonal to the first direction parallel to the bronchial wall, and
III) calculating the total maximum biopsy depth as the minimum of the first maximum biopsy depth and the second maximum biopsy depth.

The calculation of the first maximum biopsy depth is advantageously performed as $$T_{1max} = \frac{\frac{D_1}{2} - t_1}{\tan \alpha},$$

$D_1$ being the extent of the lesion in the first direction, $t_1$ being the distance of the actual biopsy point from the ideal one along the first direction, and α being the deviation of the actual biopsy direction from the ideal one along the first direction.

In an advantageous refinement, the calculation of the second maximum biopsy depth is performed as $$T_{2max} = \frac{\frac{D_2}{2} - t_2}{\tan \beta},$$

$D_2$ being the extent of the lesion in the second direction, $t_2$ being the distance of the actual biopsy point from the ideal one along the second direction, and β being the deviation of the actual biopsy direction from the ideal one along the second direction.

In at least one embodiment, the imaging method is, for example, computed tomography and/or magnetic resonance imaging and/or X-raying.

In accordance with at least one embodiment of the present invention, there is proposed a device for carrying out a method for improving the accuracy of a bronchial biopsy, comprising
an imaging device for detecting the position and extent of a lesion to be biopsied by way of imaging methods,
characterized by
a calculation element for calculating the maximum biopsy depth with a known biopsy inaccuracy as a function of the extent of the lesion and a planning element for producing a biopsy plan on the basis of the calculated maximum biopsy depth and the position of the lesion.

BRIEF DESCRIPTION OF THE DRAWINGS

Further advantages, features and properties of the present invention will now be explained in more detail with the aid of example embodiments and with reference to the accompanying drawings, in which.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1A:
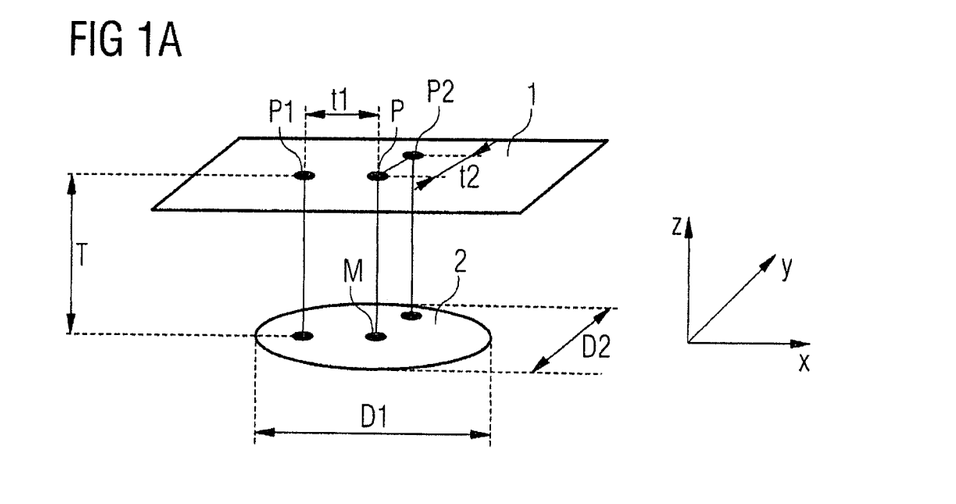
FIGS. 1a and 1b are schematics of the biopsy points and biopsy directions in the case of the biopsy of a lesion lying on a bronchial wall.

FIG. 1a is a schematic of a section of a bronchial wall 1 and a lesion 2 lying there under. Here, lesion is understood as a salient tissue feature or tissue change of any type from which tissue samples are to be removed by way of a biopsy.

Figure 1B:
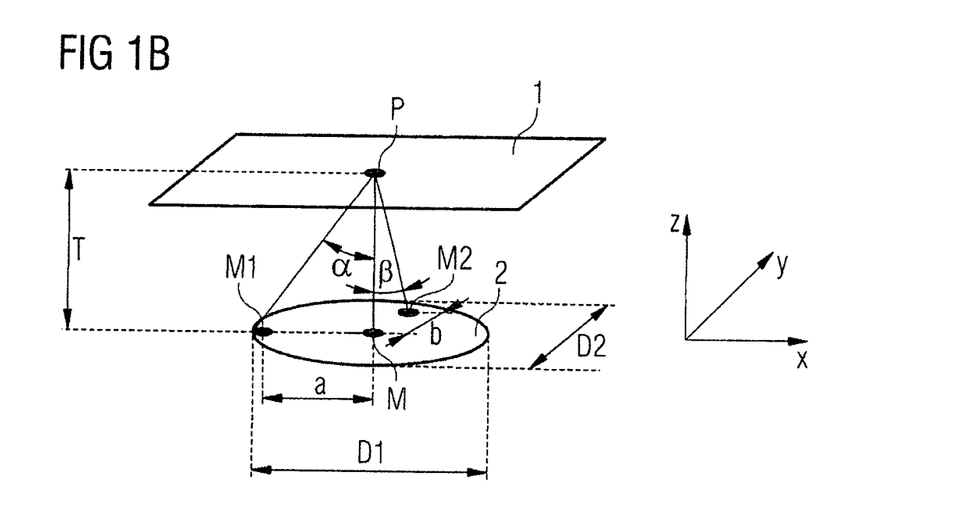

The lesion 2 is illustrated in FIGS. 1a and 1b as lying in a plane. It is assumed without restricting generality that the lesion 2 lies in a plane formed by two mutually orthogonal coordinate axes x and y, and has no further extent of any sort along the third coordinate axis z. The lesion 2 lies in this case at a depth T below the bronchial wall 1 and has in the x-y-plane, that is at a distance T from the bronchial wall, a size D1 along a first direction, here along the x-axis, and a size of D2 along a second direction, here along the y-axis.

In the case of a three-dimensional lesion, the depth T can be the distance between the bronchial wall 1 and the midpoint of the lesion 2. In this case, the sizes D1 and D2 are then the extents along the x- and the y-axes in the plane in which the midpoint of the lesion 2 also lies. Depending on the shape of the lesion, the depth T can also be defined as far as another point of the lesion 2, and so can the sizes D1, D2 in a corresponding manner. In each case, however, T is the depth to which a biopsy needle must be inserted so that a tissue sample can be removed. T is therefore the biopsy depth actually required for carrying out the biopsy.

The errors and inaccuracies occurring during a biopsy will be explained below with the aid of the illustrations of FIG. 1a and FIG. 1b. As already explained, it is assumed to this end that the lesion 2 is only two-dimensional and thus has a dimension or length $D_1$ along a first direction, here along the x-axis, parallel to the bronchial wall 1, and a second extent or width $D_2$ along a second direction, here along the y-axis, orthogonal to the first direction and parallel to the bronchial wall. In the case of an ideal biopsy, the examiner uses the bronchoscope to penetrate the bronchial wall 1 at a point P that lies directly perpendicularly above the middle M of the lesion 2, and in the case of ideal bronchoscopy, the angle between the bronchoscope and the bronchial wall 1 is exactly 90°, that is to say the bronchoscope hits the lesion 2 perpendicularly. The possible error that can arise in a real biopsy as against an ideal biopsy is composed, firstly, of a translational error and, secondly, of an angular error.

A possible translational error is illustrated in FIG. 1a. A translational error is understood as a deviation from the ideal biopsy point P, that is to say the bronchoscope penetrates the bronchial wall 1 not at the ideal point P, but at a point differing from the ideal point P. As illustrated in FIG. 1a, the bronchoscope can penetrate the bronchial wall 1 at a point $P_1$ such that a distance $t_1$ between the ideal point P and the actual point $P_1$ occurs along the x-axis. Correspondingly, the bronchoscope can penetrate the bronchial wall at a point $P_2$ that is at a distance $t_2$ from the ideal biopsy point P along the y-axis. Each deviation from the ideal biopsy point P can be illustrated as a component in the x-direction and a component in the y-direction. Assuming that the bronchoscope is held at right angles to the bronchial wall 1 during the biopsy, it is then possible to hit the lesion if it holds that:

$$t_1 < \frac{D_1}{2} \text{ and } t_2 < \frac{D_2}{2}.$$

that is to say, the lesion 2 is certainly hit during the biopsy when the deviations $t_1$ and $t_2$ in the two directions of extent of the lesion 2 are smaller than half the extents $D_1$ and $D_2$ of the lesion 2.

FIG. 1b is a schematic of the contribution of an angular error to the inaccuracy of the biopsy. Assuming that the bronchial wall 1 is penetrated by way of the bronchoscope at the ideal biopsy point P, an angular error can occur in the x-direction or the y-direction, or an angular error can occur in each further direction, and is then correspondingly composed of two components along the x- and the y-directions. In this case, the angle α in FIG. 1b shows the deviation of the actual biopsy direction from the ideal biopsy direction along the x-axis. Correspondingly, the angle β shows a deviation of the actual biopsy direction from the ideal biopsy direction along the y-axis. Each deviation in another direction can be composed of components along the two directions.

The path between the midpoint M of the lesion 2, which represents the ideal biopsy point, and the actual biopsy point $M_1$ along the x-axis is denoted in FIG. 1b by a and is yielded for a known angle α from $$a = T^* \tan \alpha.$$

The path between the midpoint M of the lesion and the actual biopsy point $M_2$ along the y-axis, which is denoted in FIG. 1b by b, is correspondingly yielded from $$b = T^* \tan \beta.$$

The point at which the lesion 2 is therefore actually hit by the bronchoscope can deviate from the ideal point because of the translational error and the angular error. The total error $f_1$ along the x-direction is therefore yielded from the distance $t_1$ and the path a as $$f_1 = t_1 + T^* \tan \alpha.$$

The error $f_2$ along the y-direction is correspondingly yielded from the distance $t_2$ and the path b as $$f_2 = t_2 + T^* \tan \beta.$$

The condition for the lesion to be hit during the biopsy is that the deviations along the two directions x and y may not be greater than half the extent of the lesion 2, that is to say the following condition holds:

$$f_1 < \frac{D_1}{2} \text{ and } f_2 < \frac{D_2}{2}.$$

The deviations α, β, $t_1$ and $t_2$ are essentially a function of at least one embodiment of the imaging method used, the accuracy of the virtual bronchoscopy, the bronchoscope used and the abilities of the examiner. In accordance with at least one embodiment of the present invention, it is therefore proposed to determine the deviations α, β, $t_1$ and $t_2$ on a phantom by way of the test series preceding the bronchoscopy. The values thus determined can then be permanently stored until there is a change in the examination conditions, for example another examiner, another bronchoscope being used, or similar. In this case of the changed examination conditions, the deviations α, β, $t_1$ and $t_2$ must be determined anew. For known deviations α, β, $t_1$ and $t_2$, it is therefore possible as a function of the extents $D_1$ and $D_2$ of the lesion 2 to calculate the biopsy depth as far as which it is possible to carry out an accurate biopsy, that is to say one with reliable hits. Assuming that a translational error and an angular error occur only along the x-direction, the maximum biopsy depth $T_{1max}$ is yielded as:

$$T_{1max} = \frac{\frac{D_1}{2} - t_1}{\tan \alpha}.$$

Correspondingly, assuming that a translational error and an angular error occur only along the y-direction of the lesion 2 the maximum biopsy depth $T_{2max}$ is yielded as:

$$T_{2max} = \frac{\frac{D_2}{2} - t_2}{\tan \beta}.$$

Since a translational error and angular error can occur in any direction in the real case, the total maximum biopsy depth $T_{max}$ is yielded as the minimum of the two calculated biopsy depths $T_{1max}$ and $T_{2max}$:

$$T_{max} = \text{Min}(T_{1max}, T_{2max})$$

Consequently, in the event of a known biopsy inaccuracy given by the parameters α, β, $t_1$ and $t_2$ it is possible to calculate as a function of the extent of the lesion 2 the depth as far as which an accurate biopsy, that is to say one hitting the lesion, can be carried out. The method in accordance with at least one embodiment of the present invention further includes a step in which the maximum biopsy depth $T_{max}$ thus calculated is compared with the actually required biopsy depth T. If the calculated maximum biopsy depth exceeds the actually required biopsy depth T, the biopsy can be carried out accurately.

Figure 2:
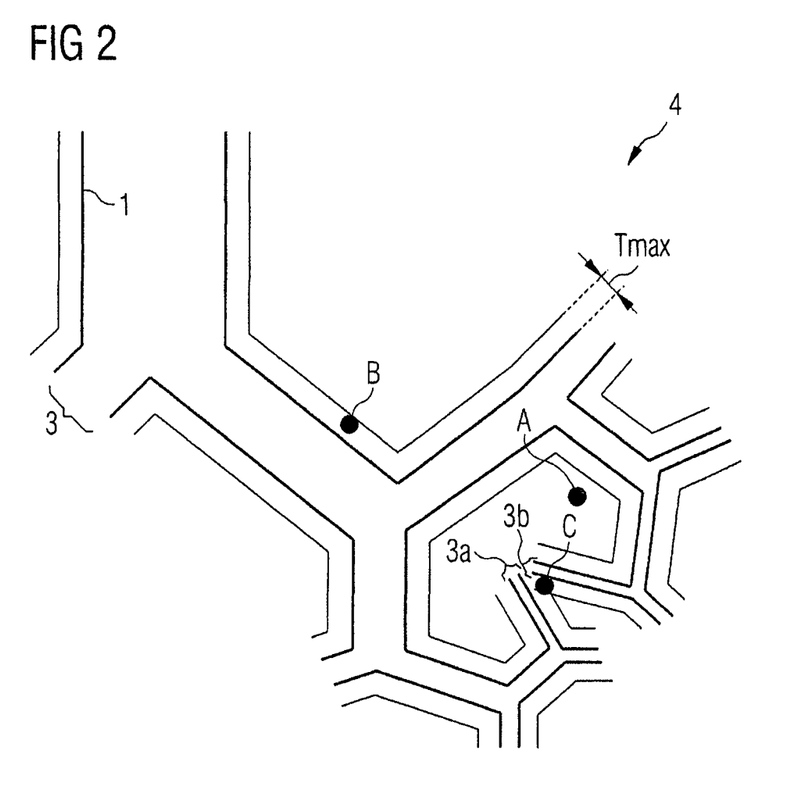
FIG. 2 is a schematic of a section of a bronchial tree with a number of lesions.

FIG. 2 is a schematic of a section of the bronchial tree 4 with three lesions A, B and C. Here, a number of bronchial branches 3 with the bronchial walls 1 are illustrated. The calculated maximum biopsy depth $T_{max}$ is illustrated as a dashed line along the bronchial walls. It is assumed here that the lesions A, B and C all have the same extents $D_1$ and $D_2$ in the present example. Thus, if the distance of one of the lesions from the bronchial wall 1 is greater than the calculated maximum biopsy depth $T_{max}$, it is impossible to carry out an accurate biopsy. In the present example, the lesion B can be reached without a problem from a bronchial branch. The lesion A, by contrast, is at a distance that is too large for an accurate biopsy that hits reliably. The lesion C can, in addition, be reached from two different bronchial branches 3a or 3b, for example.

Figure 3:
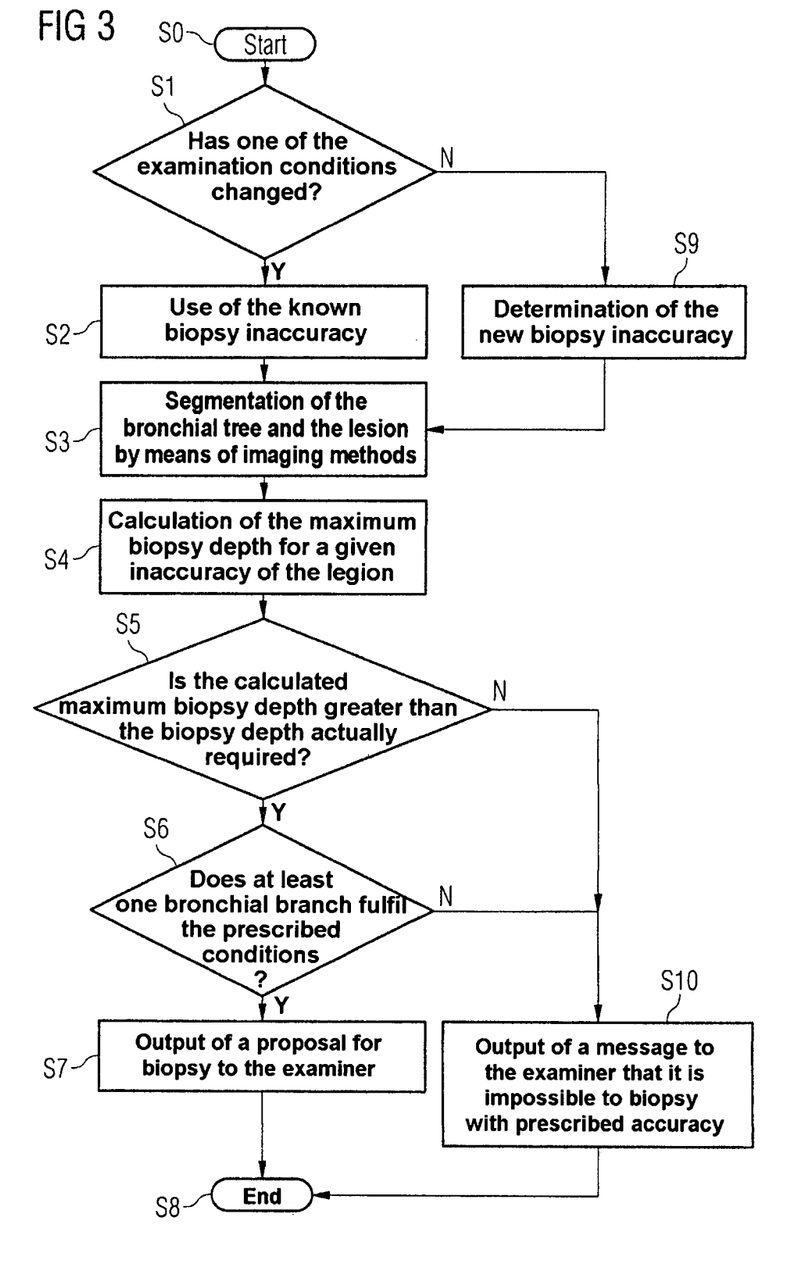
FIG. 3 is a schematic of the flow of the method in accordance with an embodiment of the present invention.

The method in accordance with at least one embodiment of the present invention is explained in more detail below with the aid of FIG. 3. The method begins in step S0. In the next step S1, a check is firstly made as to whether one of the examination conditions has changed. As already explained, the examination conditions can in this case be the type of imaging used, the accuracy of the virtual bronchoscopy, or similar. If the examination conditions have not changed, the known biopsy inaccuracy, already determined in test series and established in the parameters $\alpha$, $\beta$, $t_1$ and $t_2$, is used in step S2. Otherwise, if one of the examination conditions has changed, the biopsy inaccuracy, that is to say the parameters $\alpha$, $\beta$, $t_1$ and $t_2$, are determined anew in step S9 with the aid of test series on a phantom. In a next step S3, the bronchial tree and the lesion are recorded by way of imaging methods and segmented in order to obtain a three-dimensional display. Alternatively, the segmentation of the bronchial tree and the lesion can also be performed before the checking of the changed examination conditions in step S1.

As already explained above, in a next step S4 the maximum biopsy depth $T_{max}$ given the predetermined biopsy inaccuracy is calculated for the corresponding lesion, that is to say with reference to the extents $D_1$ and $D_2$ of the lesion 2. In a next step S5, the maximum biopsy depth $T_{max}$ thus calculated is compared with the actually required biopsy depth T and a check is made as to whether the calculated maximum biopsy depth $T_{max}$ is greater than the actually required biopsy depth T. If this condition is fulfilled, a check is made in a next step S6 as to whether at least one bronchial branch 3 fulfills the conditions for a biopsy to be carried out. If this is likewise the case, a proposal for a biopsy is output to the examiner in step S7. For example, in the virtual three-dimensional display the bronchial branch and the point that is particularly suitable for carrying out the biopsy are marked. Otherwise, if it is established in one of the steps S5 or S6 that the conditions checked there are not fulfilled, a message is output to the examiner in a step S10 to the effect that it is impossible to biopsy with the prescribed accuracy.

Figure 4:
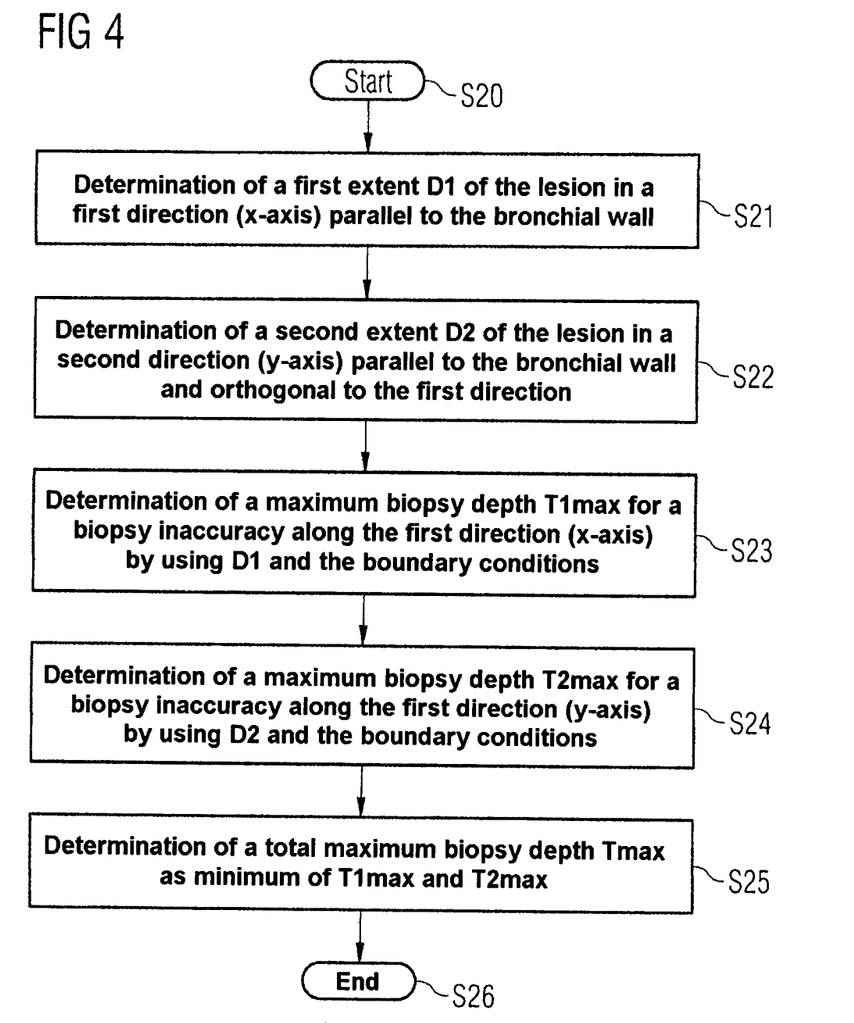
FIG. 4 is a schematic of the flow of the calculation of the maximum biopsy depth in accordance with an embodiment of the present invention.

The calculation of the maximum biopsy depth is described once again with the aid of FIG. 4. The process starts in step S20, and use is made in the following step S21 of the imaging method in order to determine the first extent $D_1$ of the lesion 2 in the x-direction parallel to the bronchial wall 1. In the next step S22, the second extent $D_2$ of the lesion is determined in the y-direction parallel to the bronchial wall 1 and orthogonal to the x-direction. In following steps S23 and S24, the respective maximum biopsy depths $T_{1max}$ are calculated as a function of the first extent $D_1$ of the lesion 2 along the x-axis, and the maximum biopsy depth $T_{2max}$ is calculated as a function of the second extent $D_2$ of the lesion 2 along the y-axis with the aid of the formulas already named. In the following step S25, the total maximum biopsy depth $T_{max}$ is then calculated as the minimum of $T_{1max}$ and $T_{2max}$. The method ends in step S26.

The principal aim in determining the biopsy plan for the examiner is whether the lesion 2 to be examined is at a distance T from the bronchial wall 1 that is greater than the calculated maximum biopsy depth $T_{max}$. Should it be possible to reach a lesion 2 from a number of bronchial branches 3, yet further factors are included in the production of the biopsy plan. For example, the diameter of the bronchial branch, the closeness of vessels that are not to be damaged, or similar can also be incorporated into the proposal. The examiner can also be supplied with a number of proposals from which he can then select one interactively. If the case occurs that the lesion 2 cannot be reliably biopsied under the prescribed conditions, this is communicated to the examiner. In this case, the examiner must seek alternatives or consciously temper the predefined error criteria.

Figure 5:
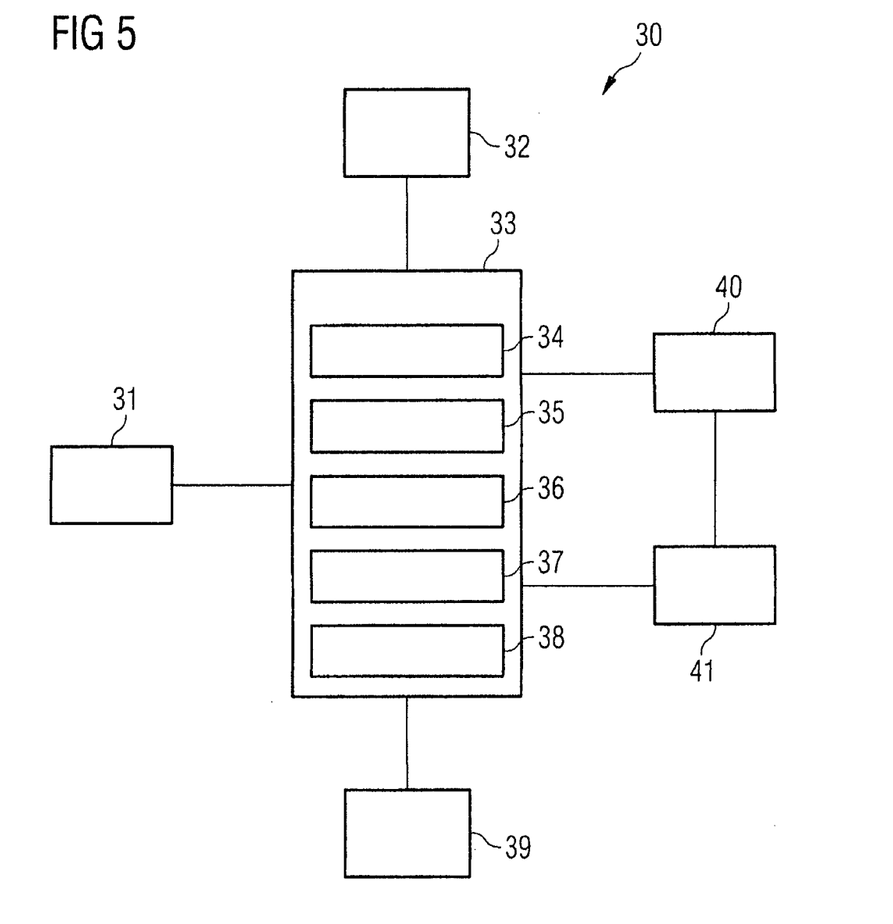
FIG. 5 shows a block diagram of the inventive device for carrying out an embodiment of the method.

FIG. 5 is a schematic of a block diagram of the inventive device 30 for carrying out at least one embodiment of the method. Via an imaging device 31 that can be a computer tomograph and/or a magnetic resonance imager and/or or an X-ray machine, the segmentation of the lesion 2 and its surroundings are undertaken by way of appropriate imaging methods in order thus to obtain a virtual three-dimensional display of the lesion 2 and of the tissue surrounding the lesion 2. The data of the imaging device 31 can then also be used to determine the position and extent $D_1$, $D_2$ of the lesion 2, as well as the biopsy depth T actually require to carry out the biopsy.

The device 30 includes a processor 33 that serves as central control unit for the device 30, for example for executing commands and fulfilling process steps. The processor 33 includes a number of elements. A first calculation element 34 serves for calculating the first maximum biopsy depth $T_{1max}$ in accordance with step S23, a second calculation element 35 serves for calculating the second maximum biopsy depth $T_{2max}$ in accordance with step S24, a calculation element 36 serves for calculating the total maximum biopsy depth $T_{max}$ in accordance with steps S4 and S25, a comparator 37 serves for comparing the total maximum biopsy depth $T_{max}$ with the biopsy depth T actually required for carrying out the biopsy in accordance with step S5, and the planning element 38 serves for producing a biopsy plan in accordance with step S6. The elements 34, 35, 36, 37 and 38 contained in the processor 33 can in this case be either functions that are loaded as software components into the main memory of the device 30 and are fulfilled in stepwise fashion by the processor, or else hardware components that are operated to carry out the calculation steps of the algorithm.

The device 30 further includes, in at least one embodiment, an input device 32, for example a keyboard, a mouse, a touchpad or the like. The examiner can thereby select a plan when choosing between a number of biopsy plans, for example. Also shown is an output device 39, for example one or more displays on which the virtual three-dimensional display of the lesion 2 and the surrounding tissue is shown. Furthermore, in accordance with step S7 the examiner is shown a proposal for a biopsy plan by way of the output device 39, a message being output to the examiner in accordance with step S10 when it is impossible to biopsy with sufficient accuracy, or a number of biopsy plans are indicated from which the examiner can then select a plan interactively by way of the input device 32, as already explained. Furthermore, a memory 40 is provided for volatile or permanent storage of data and as working memory of the device 30. A determination device 41 serves for determining the biopsy inaccuracy in accordance with step S9 with the aid of test series of a phantom, that is to say the parameters α, β, $t_1$ and $t_2$ that establish the biopsy inaccuracy are determined by the determination device.

Thus, the method in accordance with at least one embodiment of the present invention can be used under prescribed examination conditions and as a function of the extent of the lesion to be examined and of the position of the lesion in order to establish whether a lesion can be reliably hit during a biopsy. Consequently, in the case of removal of benign tissue it can be ensured that the lesion itself is benign and that, for example, it is not just that the lesion was not hit. The accuracy of the biopsy can therefore be improved by at least one embodiment of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for improving the accuracy of a bronchial biopsy, comprising:
    detecting a position and extent of a lesion to be biopsied using at least one medical imaging method;
    determining a known biopsy inaccuracy by determining a translational error and an angular error in the biopsy, the translational error being a deviation of an actual biopsy point from an ideal biopsy point, and the angular error being a deviation of an actual biopsy direction from an ideal biopsy direction;
    calculating a maximum biopsy depth with the known biopsy inaccuracy as a function of the detected extent of the lesion, the maximum biopsy depth representing a maximum depth of hitting the lesion; and
    producing a biopsy plan based on the calculated maximum biopsy depth and the detected position of the lesion.

2. The method as claimed in claim 1, wherein the producing the biopsy plan comprises comparing the calculated maximum biopsy depth with the biopsy depth actually required for carrying out the biopsy.

3. The method as claimed in claim 2, wherein the producing the biopsy plan comprises determining a bronchial branch for carrying out the biopsy when the actual biopsy depth required for carrying out the biopsy does not exceed the calculated maximum biopsy depth.

4. The method as claimed in claim 2, wherein in the producing the biopsy plan, a message is output to the examiner when the actual biopsy depth required for carrying out the biopsy exceeds the calculated maximum biopsy depth.

5. The method as claimed in claim 1, wherein the method involves a one-time determination of the biopsy inaccuracy by way of test series.

6. The method as claimed in claim 5, wherein the method involves a renewed determination of the biopsy inaccuracy in conjunction with variation of the examination conditions.

7. A method for improving the accuracy of a bronchial biopsy, comprising:
    detecting a position and extent of a lesion to be biopsied using at least one medical imaging method;
    determining a known biopsy inaccuracy by determining a translational error and an angular error in the biopsy, the translational error being a deviation of an actual biopsy point from an ideal biopsy point, and the angular error being a deviation of an actual biopsy direction from an ideal biopsy direction;
    calculating a maximum biopsy depth with the known biopsy inaccuracy as a function of the detected extent of the lesion; and
    producing a biopsy plan based on the calculated maximum biopsy depth and the detected position of the lesion, wherein the calculating the maximum biopsy depth includes,
    calculating a first maximum biopsy depth as a function of a first extent of the lesion along a first direction parallel to the bronchial wall,
    calculating a second maximum biopsy depth as a function of a second extent of the lesion along a second direction orthogonal to the first direction parallel to the bronchial wall, and
    calculating the total maximum biopsy depth as a minimum of the first maximum biopsy depth and a second maximum biopsy depth.

8. The method as claimed in claim 7, wherein the first maximum biopsy depth is calculated ($T_{1max}$) as $$T_{1max} = \frac{\frac{D_1}{2} + t_1}{\tan\alpha},$$

$D_1$ being the extent of the lesion in the first direction, $t_1$ being the distance of the actual biopsy point from the ideal one along the first direction, and α being the deviation of the actual biopsy direction from the ideal one along the first direction.

9. The method as claimed in claim 7, wherein the calculating of the second maximum biopsy depth $T_{2max}$ is calculated as $$T_{2max} = \frac{\frac{D_2}{2} - t_2}{\tan\beta},$$

$D_2$ being the extent of the lesion in the second direction, $t_2$ being the distance of the actual biopsy point from the ideal one along the second direction, and α being the deviation of the actual biopsy direction from the ideal one along the second direction.

10. The method as claimed in claim 1, wherein the at least one medical imaging method is at least one of computed tomography, magnetic resonance imaging and X-raying.

11. A device for improving accuracy of a bronchial biopsy, comprising:
    an imaging device to detect a position and extent of a lesion to be biopsied by way of at least one imaging method; and
    a calculation element to calculate a maximum biopsy depth with a known biopsy inaccuracy as a function of the detected extent of the lesion and a planning element to produce a biopsy plan based on the calculated maximum biopsy depth and the detected position of the lesion, the known biopsy inaccuracy being a translational error and an angular error in the biopsy, the translational error being a deviation of an actual biopsy point from an ideal biopsy point, and the angular error being a deviation of an actual biopsy direction from an ideal biopsy direction, the maximum biopsy depth representing a maximum depth of hitting the lesion.

12. The device as claimed in claim 11, further comprising:
a comparator to compare the calculated maximum biopsy depth with a biopsy depth actually required for carrying out the biopsy.

13. The device as claimed in claim 12, wherein the planning element is configured to determine a bronchial branch for carrying out the biopsy when the actual biopsy depth required for carrying out the biopsy does not exceed the calculated maximum biopsy depth.

14. The device as claimed in claim 12, further comprising:
an output device to output a message to the examiner when the actual biopsy depth required for carrying out the biopsy exceeds the calculated maximum biopsy depth.

15. The device as claimed in claim 11, further comprising:
a determination device for one-time determination of the biopsy inaccuracy by way of test series.

16. The device as claimed in claim 15, wherein the determination device is configured for the renewed determination of the biopsy inaccuracy in conjunction with variation of the examination conditions.

17. The device as claimed in claim 11, further comprising:
a first calculation element to calculate a first maximum biopsy depth as a function of a first detected extent of the lesion along a first direction parallel to the bronchial wall, and
a second calculation element to calculate a second maximum biopsy depth as a function of a second detected extent of the lesion along a second direction orthogonal to the first direction parallel to the bronchial wall, the calculation element being configured to calculate the total maximum biopsy depth as a minimum of the first maximum biopsy depth and the second maximum biopsy depth.

18. The device as claimed in claim 17, wherein the first calculation element is configured to calculate the first maximum biopsy depth ($T_{1max}$) as $$T_{1max} = \frac{\frac{D_1}{2} + t_1}{\tan\alpha},$$

$D_1$ being the extent of the lesion in the first direction, $t_1$ being the distance of the actual biopsy point from the ideal one along the first direction, and $\alpha$ being the deviation of the actual biopsy direction from the ideal one along the first direction.

19. The device as claimed in claim 17, wherein the second calculation element is configured to calculate the second maximum biopsy depth ($T_{2max}$) as $$T_{2max} = \frac{\frac{D_2}{2} - t_2}{\tan\beta},$$

$D_2$ being the extent of the lesion in the second direction, $t_2$ being the distance of the actual biopsy point from the ideal one along the second direction, and $\beta$ being the deviation of the actual biopsy direction from the ideal one along the second direction.

20. The device as claimed in claim 11, wherein the imaging device is at least one of a computer tomograph, a magnetic resonance imager and an X-ray machine.

21. The method as claimed in claim 3, wherein in the producing the biopsy plan, a message is output to the examiner when the actual biopsy depth required for carrying out the biopsy exceeds the calculated maximum biopsy depth.

22. The method as claimed in claim 8, wherein the calculating of the second maximum biopsy depth $T_{2max}$ is calculated as $$T_{2max} = \frac{\frac{D_2}{2} - t_2}{\tan\beta},$$

$D_2$ being the extent of the lesion in the second direction, $t_2$ being the distance of the actual biopsy point from the ideal one along the second direction, and $\beta$ being the deviation of the actual biopsy direction from the ideal one along the second direction.

23. The device as claimed in claim 13, further comprising:
an output device to output a message to the examiner when the actual biopsy depth required for carrying out the biopsy exceeds the calculated maximum biopsy depth.

24. The device as claimed in claim 18, wherein the second calculation element is configured to calculate the second maximum biopsy depth ($T_{2max}$) as $$T_{2max} = \frac{\frac{D_2}{2} - t_2}{\tan\beta},$$

$D_2$ being the extent of the lesion in the second direction, $t_2$ being the distance of the actual biopsy point from the ideal one along the second direction, and $\beta$ being the deviation of the actual biopsy direction from the ideal one along the second direction.

* * * * *